United States Patent [19]

Pomeranz

[11] Patent Number: 5,078,702
[45] Date of Patent: Jan. 7, 1992

[54] SOFT TIP CATHETERS

[75] Inventor: Mark L. Pomeranz, Newport Beach, Calif.

[73] Assignee: Baxter International Inc., Deerfield, Ill.

[21] Appl. No.: 173,493

[22] Filed: Mar. 25, 1988

[51] Int. Cl.$^5$ .................................. A61M 25/00
[52] U.S. Cl. .................................. 604/280; 604/282; 128/658
[58] Field of Search .................. 604/264, 280–282; 128/658; 138/100, 101, 118, 137; 264/139, 150, 159, 173, 248

[56]  References Cited

U.S. PATENT DOCUMENTS

| | | |
|---|---|---|
| 3,485,234 | 12/1969 | Stevens . |
| 3,585,707 | 6/1971 | Stevens . |
| 3,890,976 | 6/1975 | Bazell et al. ............... 128/207.15 |
| 4,120,352 | 10/1978 | Husson ............................ 165/173 |
| 4,239,042 | 12/1980 | Asai . |
| 4,321,226 | 3/1982 | Markling . |
| 4,385,635 | 5/1983 | Ruiz ................................. 128/658 |
| 4,402,684 | 9/1983 | Jessup . |
| 4,425,919 | 1/1984 | Alston, Jr. et al. ............. 604/282 |
| 4,531,943 | 7/1985 | Van Tassel et al. . |
| 4,547,193 | 10/1985 | Rydell ............................. 128/658 |
| 4,551,292 | 11/1985 | Fletcher et al. ................ 604/280 |
| 4,563,181 | 1/1986 | Wijayarathna et al. . |
| 4,577,543 | 3/1986 | Wilson ............................. 604/280 |
| 4,596,563 | 6/1986 | Pande . |
| 4,636,346 | 1/1987 | Gold et al. . |
| 4,665,604 | 5/1987 | Dubowik ......................... 604/282 |
| 4,665,604 | 5/1987 | Dobowik . |
| 4,697,705 | 10/1987 | Garganese ....................... 206/488 |
| 4,748,204 | 5/1988 | Kawashima et al. ............. 525/64 |
| 4,764,324 | 8/1988 | Burnham ......................... 264/150 |
| 4,782,834 | 11/1988 | Maguire et al. ................. 604/280 |
| 4,801,297 | 1/1989 | Mueller ........................... 604/280 |
| 4,842,590 | 6/1989 | Tanabe et al. ................... 604/282 |
| 4,863,442 | 9/1989 | DeMello et al. ................ 604/282 |
| 4,886,506 | 12/1989 | Lovgren et al. ................. 604/282 |
| 4,898,591 | 2/1990 | Jang et al. ....................... 604/264 |

Primary Examiner—Stephen C. Pellegrino
Assistant Examiner—Ralph A. Lewis
Attorney, Agent, or Firm—Michael C. Schiffer; Sandra S. Schultz

[57]  ABSTRACT

Catheters having tubular body portion formed with an inner sheath of a rigid polymeric material encapsulated by an outer sheath formed of the same or different rigid polymeric material. A wire braid is embedded in the tubular body between the inner and outer sheaths. The catheter further includes a tip portion which is welded to an end of the tubular body portion. This tip portion has an inner sheath of a rigid polymeric material encapsulated by an outer sheath of a flexible polymeric material. The inner sheath of both the body and tip portions are formed from the same polymeric material. The compatibility between the polymeric materials of the inner sheaths substantially increases the bonding between the tip and body portions of the catheter to form a stable joint.

29 Claims, 1 Drawing Sheet

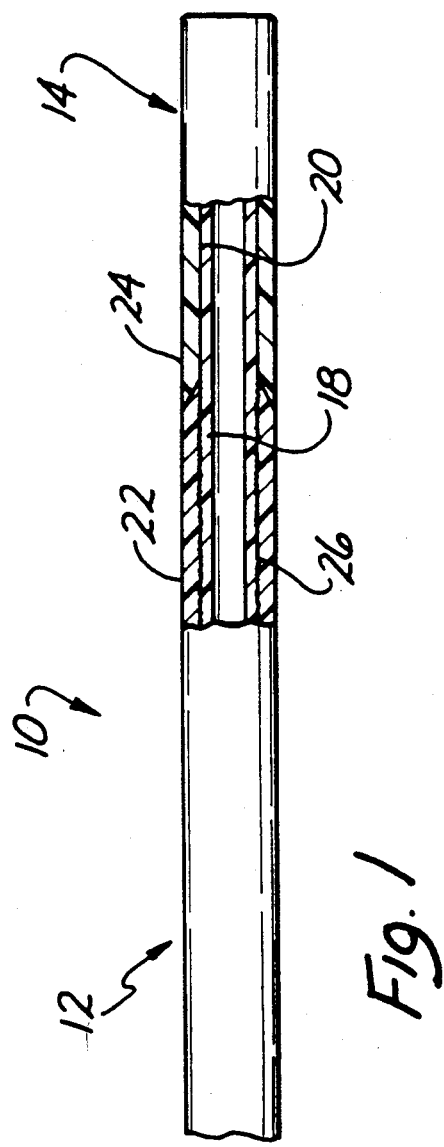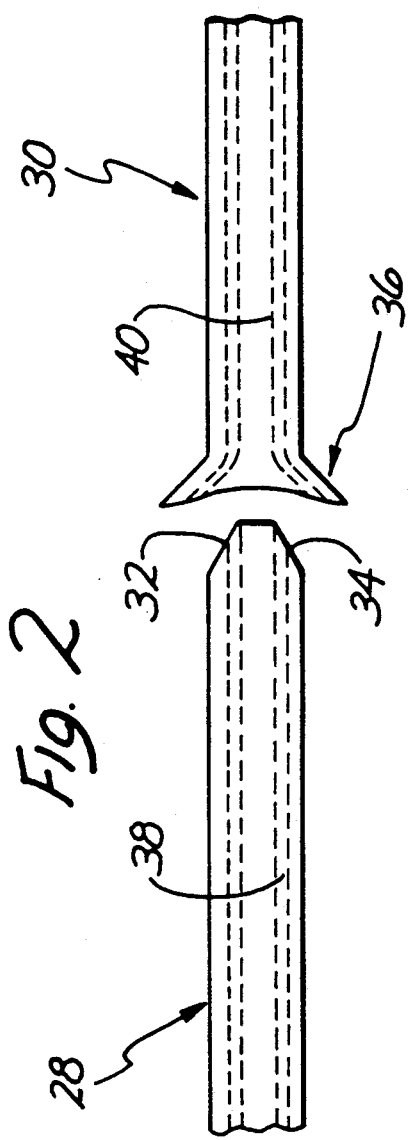

SOFT TIP CATHETERS

BACKGROUND OF THE INVENTION

The present invention is directed to catheters and methods of manufacturing the same. In particular, the present invention is directed to soft tip catheters.

Catheters are used in various types of surgical procedures. For example, catheters may be used to deliver solutions to specific bodily areas, e.g for coronary angiography, or are constructed to act as guideways through which other catheters are directed to specific body locations. Irrespective of their ultimate usage, catheters are inserted and pushed through a particular a body vessel, e.g. a blood vessel. In order to easily pass through such a vessel the catheter is constructed to exhibit certain physical characteristics. That is, the catheter must possess specific physical properties to facilitate the insertion and passage through the vessel.

More particularly, the catheter should possess sufficient strength without being too stiff to facilitate the passage of the catheter through the vessel. Generally, a catheter is pushed through a vessel by twisting the catheter which moves the catheter along the vessel by a recoilling motion. Thus in order to facilitate this twisting movement through the vessel the catheter must have longitudinal flexibility, while also being somewhat rigid to provide for a high degree of torsional control.

While a rigid catheter provides the desired high torsional control, this rigidity of the catheter increases the potential of damaging the vessel as it travels through the vessel. In particular, the distal end, or tip, of a rigid catheter may puncture, or in some other manner damage the vessel through which it is travelling, or may cause damage to an organ in which it comes into contact.

Accordingly, catheters have been designed to possess a soft or flexible distal tip. This flexible tip minimizes the potential of damaging an organ or vessel by the catheter, while the rigid catheter body ensures movement through the vessel. Examples of such soft tip catheters ar well known.

One such soft tip catheter is disclosed in U.S. Pat. No. 4,402,684 issued to Jessup, wherein the catheter is formed with a soft outer sheath defining a lumen in which a stylete is positioned. This stylete subdivides the lumen into multiple pathways. By forming the stylete from a rigid polymeric material the desired rigidity is imparted to the catheter, while the outer surface of such a catheter remains soft to minimize damage to the vessel or organs it comes into contact with. However, the disclosed catheter is not suitable for forming a guide catheter in that the guide catheter lumen must remain open and thus could not contain the rigid stylete.

Other types of presently available soft tip catheters are manufactured by fusing a flexible tubular member to the distal end of the rigid catheter body. Examples of these types of catheters are disclosed in U.S. Pat. Nos. 4,563,181 issued to Wijayarathna et al; 3,485,234 and 3,585,707 both issued to Stevens; 4,321,226 issued to Markling; 4,531,943 issued to Van Tassel et al; and 4,665,604 issued to Dobowik. This type of catheter is also disclosed in U.S. patent application Ser. No. 946,491, filed on Dec. 23, 1986, and assigned to the same assignee of the instant application.

All of the catheters disclosed in this various patents fuse the soft tip to the end of the catheter body, typically using a lap joint fusing process, as disclosed in Markling, Dubowik and Stevens. While these types of catheters are advantageous in providing a soft distal tip for insertion into the vessel first, such catheters do possess certain disadvantages.

The basic disadvantage with these presently available catheters is the incompatibility between the polymers forming the soft pliable tip portion and the catheter body. This incompatibility reduces the resulting joint between the two fused together portions, even when the catheter is construction using a lap joint. This weak joint results from the incompatibility between the polymeric materials forming the catheter body and tip portions. That is, the body portion, is formed from a rigid polymer, while the tip portion is formed from another more elastic polymer, with these two different polymers reducing the bonding between the two portions to such a degree that even when the body and tip portions are properly bonded together a relatively weak joint results.

This particular disadvantage caused by the use of two different polymers was specifically recognized in Wijayarathna et al. This patent specifically discloses a tip formed from a polyether-polyamide material which is at least partially compatible with the polyamide (nylon) material forming the catheter body. The polyamide constituent of the polyether-polyamide material used to prepare the tip portion increases the bonding between the two portions, but still does not provide the type of bonding which would result from using the same two materials.

The major reason for existence of this type of disadvantage is that those polymers which have the characteristic of forming a rigid structure are not suitable for forming a soft catheter tip. As a result other methods of forming catheters to possess a soft tip have been developed to overcome the weak joint formed between the catheter tip and body portion with the above discussed catheters.

One particular method involves forming the catheter with two sheaths, an inner sheath formed from a rigid material and an outer sheath formed from a more flexible material. By extending the outer sheath beyond the inner sheath the catheter is provided with an integral soft tip. Examples of such catheters is disclosed in U.S. Pat. Nos. 4,239,042 issued to Asai and 4,596,563 issued to Pande.

Another type of catheter construction is disclosed in U.S. Pat. No. 4,636,346 issued to Gold et al. This catheter includes three sheaths, and inner sheath formed from polytetrflouroethylene (PTFE), an intermediate sheath formed from a rigid polymeric material and an outer sheath formed from a more flexible polymeric material. In order to form a more flexible tip portion the intermediate sheath is removed from the distal portion of the catheter. The disadvantage with this catheter design is that the PTFE inner sheath does not form an adequate bond with the outer sheath, thus forming a weak joint which may fail.

The major concern with the weak bonding joint found in the above discussed catheters is that failure along the fused joint between the catheter tip and body portions, while the catheter remains in the patient's body has obvious determental consequences to the patient. However, any proposed catheter construction must also maintain a soft tip portion, which heretofore has ruled out the use of rigid polymeric polymers in the tip area.

SUMMARY OF THE INVENTION

The present invention overcomes the above discussed disadvantages by a novel catheter construction. The catheters of the invention include a tubular body portion having a inner layer of a rigid polymeric material and an outer layer of a rigid polymeric material. A wire braid, or other suitable stiffening means, is preferably embedded in the tubular body between the two different layers. The catheter further includes a tip section which is welded to an end of the tubular body portion. This tip section also includes two layers, a first inner layer of a rigid polymeric material and an outer layer of a flexible polymeric material. The inner rigid layer is formed from the same polymeric material used to form the inner layer of the tubular body. This compatibility between the polymeric materials of the two inner layers of the body portion and the tip section substantially increases the bonding at the formed joint.

A unexpected advantage in forming the tip section with a rigid polymeric inner layer is an increase in the structural integrity of the tip section, that is the tip portion possess transverse rigidity. This increase in structural integrity further increase the handling characteristics of the catheter by increasing the torsional force. Nevertheless, the use of the more rigid polymeric inner layer overlaid with the soft pliable polymeric material maintains the desired flexibility in the tip portion. That is the pliable polymeric material forming the outer layer of the tip minimizes the potential of trauma to a bodily cavity through which the catheter is directed.

DESCRIPTION OF THE DRAWINGS

The present invention may be better understood and the advantages will become apparent to those skilled in the art by reference to the accompanying drawings, wherein like reference numerals refer to like elements in the several figures and wherein:

FIG. 1 is a side partially cut-away view of a catheter of the invention; and

FIG. 2 is a side exploded view of a catheter illustrating separately the body portion and tip section prior to fusing the two together in accordance with an embodiment of the invention.

DESCRIPTION OF THE INVENTION

The present invention is directed at soft tip catheters in general, and specifically at soft tip catheters having a stronger fused joint. More particularly, the present invention includes a body portion and tip section formed with inner layers or sheaths prepared from the same rigid polymeric material. When the body portion and tip section are fused together these compatible polymeric materials enhance the fusion at the formed joint.

Generally, the catheters of the invention are elongated tubular members having at least one lumen through which fluids, wiring for electrical devices positioned downstream in the catheter, or other diagnosistic catheters may be directed to a specific area of a patient's body. The present invention will be described by reference to a guide catheter, however it is to be understood that the present invention is applicable to any other type of catheter. In accordance with the illustrated embodiment the catheter will possess a single lumen through which another catheter, typically a diagnostic catheter, will pass.

A catheter, one of which is seen generally in FIG. 1 at 10, includes a body section, seen generally at 12 to which is fused a tip portion, seen generally at 14. While the illustrated soft tip portion 14 is straight, it should be noted that it is customary to form catheters with tip portions 14 having one or more bends. These bends enhance the ability of fitting the catheter into a specific artery or vein, depending upon the particular operational procedure being performed by the surgeon. The type of bends, as well as the method of forming such bends is not critical to the invention, and will not be discussed any further herein.

The catheter tip portion 1 is constructed to be soft and pliable, but also to maintain physical integrity with the body section 12 after being fused thereto. This is accomplished by forming the tip portion 14 and body section 12 with compatible portions which fuse together more successfully. In particular, the body section 12 and tip portion 14 both include inner sheaths, seen respectively at 18 and 20, which are formed from the same polymeric material. In this fashion when the section 12 and portion 14 are fused together these inner sheaths 18 and 20 flow together and in essence form a single polymeric sheath. The joint formed between the body section and tip portion is thus stronger than found in presently available catheters.

The polymeric material from which the inner sheaths 18 and 20 are formed includes those thermoplastic polymers which form substantially rigid structures. These rigid polymeric materials provide the resulting structure with transverse rigidity, but longitudinal flexibility. In general, these types of polymers include polyamides, polyethylene terephthlates (PET), polyacetals, polycarbonates and polyether/polyamide co-polymers. These polymers provide the desired transverse rigidity, while also providing longitudinal flexibility. This ensures that the resulting catheter will provide high torsional control when it is inserted into a vessel. This will allow the surgeon to move the catheter through a specific vessel, i.e. a vein, by conventional techniques.

The body section 12 and tip portion 14 further include outer layers or sheaths, seen respectively at 22 and 24. The outer sheath 22 of the body section 12 will also be formed from a rigid polymeric material, and may be formed from the same polymeric material forming the inner sheath 18.

In order to further increase the rigidity of the body section 12, a stiffening material 26 is embedded between the body section inner and outer sheaths 18 and 22. This stiffening material will typically be one or more wires wound about the inner sheath 18, and more preferably a wire braid embedded between the sheaths 18 and 22.

Unlike the body section 12, the tip portion outer sheath 24 is formed from a soft pliable polymeric material. Generally, this soft pliable polymeric material is deposited, e.g. by an extrusion technique, over the inner sheath 20. Examples of soft pliable polymeric materials include the various soft thermoplastic polyolefins (polyethylene and polypropylene), polyurethanes, polyesters and other suitable thermoplastic polymers. It should be noted that the polymers used to form the various inner and outer sheaths should also be non-thrombogenic, that is biologically compatible materials.

By "rigid polymeric material" it is meant a polymer which will form a layer having a sufficient shore hardness to provide the desired transverse rigidity and longitudinal flexibility to obtain the necessary torsional control. Typically a shore hardness from about D50 to about D80, preferably a shore hardness of D55 or D63.

By "soft pliable polymeric material" it is meant a polymer which will render the outer sheath of the tip portion 14 flexible and soft enough to avoid trauma to a bodily cavity through which the catheter passes. Typically this polymeric material will have a shore hardness from about D25 to about D50, preferably a shore hardness of D35 or D40.

The described polymeric materials will provide the body section 12 and tip portion 14 with the desired physical characteristics. In particular, the described polymeric materials will provide the body section 12 with the desired transverse rigidity, while maintaining the desired lengthwise flexibility. The tip portion 14 will also have some transverse rigidity, but will have the desired softness at the exposed outer surface.

The tip portion 14 transverse rigidity is dependent upon the thickness of the inner sheath 20. That is, the rigidity of the inner sheath 20 effects the overall rigidity of the tip portion 14, and as such the thickness of the polymeric material forming the sheath 20 should be selected depending upon the desired end use of the catheter. It should be noted that a minimum thickness is necessary in order to ensure a proper fusion between the tip portion inner sheath 20 and the body section inner sheath 18. In this regard, the tip portion inner sheath 20 should generally have a thickness of from about 0.004 inch to about 0.010 inch, preferably from about 0.005 inch to about 0.008 inch.

Furthermore, the thickness of each of the respective inner and outer sheaths should be selected to provide that the overall wall thickness of the catheter is from about 0.008 inch to about 0.020 inch. The precise thickness depends upon the desired use of the catheter. That is, the particular use of the catheter will dictate the diameter of the lumen, in the case of a guide catheter, or of combined transverse area of one or more lumens for other types of catheters. Since it is always desireable to minimize the overall outer diameter of the catheter, the selected diameters of the lumens, as well as the thickness of the respective sheaths should be maintained to provide for the smallest possible outer diameter.

In general, guide and angiography catheters should possess outer diameters of from about four (4) to about fourteen (14) french, preferrably outer diameters of 7, 8, or 9 french for guide catheters and outer diameters of 5, 6, 7, or 8 french for angiography catheters (with each french unit being equivalent to 0.013 of an inch). The inner diameter of the single lumen of a guide catheter should be from about 0.012 inch to about 0.166 inch, preferably from about 0.022 inch to about 0.152 inch.

The catheters of the invention may be constructed according to any suitable technique. In particular, the catheter of the invention may be formed by any known technique for fusing or welding the tip portion to an end of the body section.

Generally, the body section 12 and tip portion 14 are individually produced using standard extrusion techniques. Typically, the polymeric material selected for forming the inner sheaths 18 and 20 is separately extruded upon a cylinderical mandrel, i.e. wire, to form the respective sheaths 18 and 20 of a desired thickness. If desired a stiffening material, i.e. wire sheath, is wrapped about the formed body section inner sheath 18. Finally, the respective outer sheaths 22 and 24 are formed by extruding the specifically selected polymeric material upon the now formed inner sheaths 18 and 20.

The welding of the body section 12 and tip portion 14 may be performed in accordance with any of the available techniques. For example, that end of the body section 12 which is to function as the distal end may be machined to remove the outer sheath 22 for a short distance. That end of the tip portion 14, which is to be welded to the body section 12 end is widened by any suitable method, such as, by insertion of a heated mandrel into the respective end which causes the end to expand to the outer diameter of the heated mandrel. This now expanded end is then placed over the ground down end of the body section 12 and welded in place.

The preferred construction method will now be described with reference to FIG. 2, wherein a preformed body section and preformed tip portion are seen at 28 and 30. The manner in which such section 28 and portion 30 are formed is as described above, or in accordance with any suitable technique. That end of the body section 28 which will be fused to the tip portion 30 is machined to provide sloping surfaces 32 and 34. These sloping surfaces 32 and 34 position the inner sheath 38 as the leading end of the body section 28, thus ensuring the proper fusing between the body section inner sheath 38 and the tip portion inner sheath 40. Further, the proper end of the tip portion 30 is formed to flare outwards, as seen as flared end 36. The inside diameter of flared end 36 is sufficient to fit over the sloping surfaces 32 and 34. Thus the polymeric material of the inner sheaths 38 and 40 can be placed into intimate contact.

The respective ends of the body section 28 and tip portion 30 are then welded together by any suitable technique, e.g. radio frequency (RF), chemical or ultrasonic welding. One specific RF welding technique and suitable device is disclosed in U.S. Pat. No. 4,574,173, which disclosure is incorporated herein by reference. Once the welding process is completed any excess polymeric material may be removed from the outer surface of the catheter.

As stated the invention may be used for any type of catheter and has only been described by way of illustration for a guide catheter. Accordingly, even though the catheter 10 is illustrated with a single lumen 42, the catheter of the invention may include two or more appropriately dimensioned lumens, not shown.

While the preferred embodiments have been described, various modifications and substitutions may be made thereto without departing from the scope of the invention. Accordingly, it is to be understood that the invention has been described by way of illustration and not limitation.

What is claimed is:

1. A catheter comprising:
   a tubular body portion formed from a rigid polymeric material; and
   a tubular tip portion comprising an outer layer formed from a soft and pliable polymeric material and an inner layer formed of a rigid polymeric material substantially the same as said rigid polymeric material forming said tubular body portion, and wherein said tubular tip portion is fitted to an end of said tubular body portion by fusing said tip portion inner layer to said body portion to form a lap joint.

2. A catheter according to claim 1 and wherein:
   said rigid polymeric material is selected from the group consisting of polyamides, polyethylene terphthalates, polyacetals, polycarbonates and polyether/polyamide copolymers.

3. The catheter of claim 2 wherein said body portion is formed of an inner and outer sheath formed from a rigid polymeric material.

4. The catheter of claim 3 wherein said rigid material from which said tubular body portion inner and outer sheaths are formed are the same.

5. The catheter of claim 4 wherein said rigid polymeric material is of the type having a shore hardness of from about D50-D80.

6. The catheter of claim 5 wherein said soft, pliable polymeric material is of the type having a shore hardness of from about D25 to about D50.

7. The catheter of claim 6 further including a stiffening means embedded between said two rigid polymeric material sheaths.

8. The catheter of claim 4 further including a stiffening means embedded between said two rigid polymeric material sheaths.

9. The catheter of claim 3 wherein said rigid material from which said tubular body portion inner and outer sheaths are formed are different.

10. A catheter comprising:
a tubular body portion including inner and outer sheaths individually formed from one or more rigid polymeric materials selected from the group consisting of polyamides, polyethylene terephthalates, polyacetals, polycarbonates and polyether/polyamide copolymers, and a stiffening means wound around said inner sheath; and
a tip portion comprising an inner sheath of rigid polymeric material and an outer sheath of a flexible polymeric material, wherein said inner rigid sheath is comprised of a polymeric material substantially the same as said polymeric material forming said inner sheath of said tubular body, with said inner sheath of said tip portion fused to said tubular body portion to form a lap joint.

11. The catheter of claim 10 wherein said rigid material from which said tubular body portion inner and outer sheaths are formed are the same.

12. The catheter of claim 11 wherein said rigid polymeric material is of the type having a shore hardness of from about D50-D80.

13. The catheter of claim 12 wherein said soft, pliable, flexible polymeric material is of the type having a shore hardness of from about D25 to about D50.

14. The catheter of claim 11 wherein said rigid polymeric material is of the type having a shore hardness of D55 or D63.

15. The catheter of claim 14 wherein said flexible polymeric material is of the type having a shore hardness of D35 or D40.

16. The catheter of claim 10 wherein said rigid material from which said tubular body portion inner and outer sheaths are formed are different.

17. The catheter of claim 16 wherein said rigid polymeric material of said inner and outer sheaths are of the type having a shore hardness of from about D50-D80.

18. The catheter of claim 17 wherein said soft, pliable, flexible polymeric material is of the type having a shore hardness of from about D25 to about D50.

19. The catheter of claim 16 wherein said rigid polymeric material of said inner and outer sheaths are of the type having a shore hardness of D55 or D63.

20. The catheter of claim 19 wherein said flexible polymeric material is of the type having a shore hardness of D35 or D40.

21. A catheter according to claim 10 and wherein said flexible polymeric material is selected from the group consisting of polyethylenes, polypropylenes, polyurethanes, and polyesters to aid in bonding of the inner tip sheath to the outer tip sheath.

22. A catheter comprising:
a tubular body portion having at least a first passageway traversing therethrough from opposite ends, said tubular body portion being formed with an inner sheath of rigid polymeric material selected from the group consisting of polyamides, polyethylene terephthalates, polyacetals, polycarbonates, and polyether/polyamide copolymers having Shore hardness in the range of about D50 to about D80, upon which a stiffening means is wound, said tubular body portion further being formed with an outer sheath disposed over said stiffening means and said inner sheath which is formed from a second rigid polymeric material selected from the group consisting of polyamides, polyethylene terephthalates, polyacetals, polycarbonates, and polyether/polyamide copolymers having Shore hardness in the range of about D50 to about D80;
a tubular shaped tip portion which has at least a first passageway traversing therethrough, said passageway opening at least at a first end of said tip portion, said tubular tip portion having an inner sheath formed from a rigid polymeric material substantially the same as said rigid polymeric material forming either said inner or outer sheaths of said tubular body portion and an outer sheath disposed upon said inner sheath formed from a soft pliable polymeric material selected from the group consisting of polyethylene, polypropylene, polyurethanes, and polyesters having Shore hardness of about D25 to about D50, said tubular shaped tip portion forming a lap joint with said tubular body portion with said tip portion inner sheath fused directly to said body portion and wherein said tip portion passageway communicates with said body portion first passageway.

23. The catheter of claim 22 wherein said rigid polymeric material forming said inner and outer sheaths of said body portion are the same polymeric material.

24. The catheter of claim 23 wherein said rigid polymeric material is of the type having a shore hardness of from about D50-D80.

25. The catheter of claim 23 wherein said rigid polymeric material is of the type having a shore hardness of D55 or D63.

26. The catheter of claim 25 wherein said soft pliable polymeric material is of the type having a shore hardness of D35 or D40.

27. The catheter of claim 22 wherein said rigid polymeric material forming said inner and outer sheaths of said body portion are different polymeric materials.

28. The catheter of claim 27 wherein said rigid polymeric material of said inner and outer sheaths are of the type having a shore hardness of D55 or D63.

29. The catheter of claim 28 wherein said soft pliable polymeric material is of the type having a shore hardness of D35 or D40.

* * * * *